United States Patent
Dulaff (10) Patent No.: US 10,107,668 B2
(45) Date of Patent: Oct. 23, 2018

(54) FLUID CONTAINERS WITH INTEGRATED LEVEL SENSING

(71) Applicant: Siemens Healthcare Diagnostics Inc., Tarrytown, NY (US)

(72) Inventor: Paul Dulaff, Columbia, NJ (US)

(73) Assignee: Siemens Healthcare Diagnostic Inc., Tarrytown, NY (US)

( * ) Notice: Subject to any disclaimer, the term of this patent is extended or adjusted under 35 U.S.C. 154(b) by 208 days.

(21) Appl. No.: 15/109,405

(22) PCT Filed: Jan. 8, 2015

(86) PCT No.: PCT/US2015/010695
§ 371 (c)(1),
(2) Date: Jun. 30, 2016

(87) PCT Pub. No.: WO2015/106030
PCT Pub. Date: Jul. 16, 2015

(65) Prior Publication Data
US 2016/0320222 A1    Nov. 3, 2016

Related U.S. Application Data

(60) Provisional application No. 61/925,566, filed on Jan. 9, 2014.

(51) Int. Cl.
*G01F 23/26* (2006.01)
*B01L 3/00* (2006.01)
(Continued)

(52) U.S. Cl.
CPC .............. *G01F 23/268* (2013.01); *B01L 3/52* (2013.01); *G01F 23/265* (2013.01);
(Continued)

(58) Field of Classification Search
None
See application file for complete search history.

(56) References Cited

U.S. PATENT DOCUMENTS 4,002,996 A * 1/1977 Klebanoff ........... A61M 5/1684
137/392
4,099,167 A * 7/1978 Pomerantz ............ G01F 23/265
340/620
(Continued)

FOREIGN PATENT DOCUMENTS

DE      10 2007 001175 A1   7/2008
EP         0 658 431 B1     5/2000
FR         2 765 334 A1    12/1998

OTHER PUBLICATIONS

PCT International Search Report and Written Opinion dated Apr. 13, 2015 (10 Pages).

(Continued)

Primary Examiner — Paul West
Assistant Examiner — Mark A Shabman (57) ABSTRACT

Electrodes are integrated into a container design for fluid level detection in the container. The electrodes have a conductive surface, and an adhesive backing may be attached opposite the conductive surface to secure the electrodes to the container. Electrical contact to each conducting surface is made to a detection circuit to obtain a fluid level. A radio-frequency identification (RFID) tag may be incorporated onto the container along with the level detection circuit to record the container history, such as last used time event, net evaporation during storage, re-suspension performance after storage, number of agitation cycles, instrument serial number, date opened/accessed, and other desirable information.

25 Claims, 6 Drawing Sheets

(51) Int. Cl.
   *G01N 35/00* (2006.01)
   *G01N 35/10* (2006.01)
(52) U.S. Cl.
   CPC . *B01L 2200/143* (2013.01); *B01L 2300/0645* (2013.01); *G01N 2035/00782* (2013.01); *G01N 2035/1025* (2013.01)

(56) References Cited

U.S. PATENT DOCUMENTS

| | | | | |
|---|---|---|---|---|
| 4,295,370 A | | 10/1981 | Bristol | |
| 4,749,988 A | * | 6/1988 | Berman | G01F 23/268 |
| | | | | 340/618 |
| 6,164,744 A | * | 12/2000 | Froger | B41J 2/1752 |
| | | | | 347/7 |
| 2005/0132796 A1 | * | 6/2005 | Brookner | G01F 23/284 |
| | | | | 73/290 R |

OTHER PUBLICATIONS

Extended EP Search Report dated Jan. 5, 2017 of corresponding European Application No. 15735391.3, 4 Pages.

* cited by examiner

FLUID CONTAINERS WITH INTEGRATED LEVEL SENSING

CROSS REFERENCE TO RELATED APPLICATIONS

This application claims priority to U.S. provisional application Ser. No. 61/925,566 filed Jan. 9, 2014, which is incorporated herein by reference in its entirety.

TECHNOLOGY FIELD

The present disclosure relates to a low cost, high resolution, and reliable fluid level detection system for fixed and removable, portable fluid containers.

BACKGROUND

Fluid level detection in containers has traditionally been approached by using container weight, mechanical measurement of fluid height, or by resulting capacitance that the container represents when measured. These approaches can be costly, and may result in questionable accuracy and reliability of measurement. Also, the container, if removable, must be placed on the instrument to determine the amount of fluid contained therein, which can add time to time-sensitive procedures.

Capacitance level sense of fluids has a strong technical foundation, since fluids (particularly water) have a much higher dielectric constant as compared to air or vacuum, and yield a strong signal. Capacitance level sense of removable, portable containers has the challenge of maintaining high accuracy and resolution when using external plates or electrodes. These electrodes, when contacting the outer surfaces of containers, cannot securely and consistently contact the outside of the container. Typically, an air gap between the container and the electrode introduces errors.

Therefore, a low cost, high resolution, and reliable fluid level detection system for fixed and/or removable, portable fluid containers is desired.

SUMMARY

Embodiments are directed to a fluid container and a fluid level detection system and method for fluid containers.

According to an embodiment, a fluid container for fluid level detection comprises: one or more level sensor electrodes, each secured to a respective outer portion of the container; and a common electrode secured to a second outer portion of the container, the second outer portion of the container opposite at least a portion of each of the respective outer portions of the one or more level sensor electrodes. Each of the electrodes comprises a conductive surface; and the container is configured to come into contact with a circuit configured to apply a power source across one of the one or more level sensor electrodes and the common electrode to detect a level of fluid contained in the container corresponding to the one of the one or more level sensor electrodes.

In an embodiment, the container includes a plurality of compartments, and the one or more level sensor electrodes comprise a plurality of level sensor electrodes, each secured on the container to correspond to a respective one of the plurality of compartments.

In an embodiment, the one or more level sensor electrodes and the common electrode each comprise a contact to which the power source is applied.

In an embodiment, the conductive surfaces each comprise a thin sheet with a conductive coating applied thereto.

According to an embodiment, each of the one or more level sensor electrodes and the common electrode comprises an adhesive backing opposite the conductive surface, and each of the one or more level sensor electrodes and the common electrode is secured to the container with the adhesive backing.

In another embodiment, the container also includes one or more radio-frequency identification tags, each embedded in a respective one of the one or more level sensor electrodes to identify the respective one of the one or more level sensor electrodes. In an embodiment, the one or more radio-frequency identification tags is embedded in respective contacts of the one or more level sensor electrodes.

In an additional embodiment, the one or more level sensor electrodes comprise a plurality of level sensor electrodes, the plurality of level sensor electrodes arranged in a substantially horizontal configuration along the container; and contact with the circuit applying the power source detects a dielectric constant at a horizontal position of the container corresponding to the level sensor electrode at which the power source is applied. In an embodiment, the container also includes a plurality of compartments, each with an associated one of the plurality of level sensor electrodes, wherein the detection of the dielectric constant at the horizontal position comprises detection in one of the plurality of compartments corresponding to the associated one of the plurality of level sensor electrodes to which the power source is applied.

According to an embodiment, a fluid level detection system for fluid containers comprises: a container configured to hold one or more fluids; one or more level sensor electrodes, each secured to a respective outer portion of the container; a common electrode secured to a second outer portion of the container, the second outer portion of the container opposite at least a portion of each of the respective outer portions of the one or more level sensor electrodes; and a detection circuit configured to apply a power source across one of the one or more level sensor electrodes and the common electrode to detect a level of fluid of the one or more fluids contained in the container corresponding to the one of the one or more level sensor electrodes. Each of the electrodes comprises a conductive surface.

According to an embodiment, a method of detecting a fluid level in a container, comprises: applying a power source across a level sensor electrode and a common electrode, the level sensor electrode secured to a first outer portion of the container and the common electrode secured to a second outer portion of the container, the second outer portion of the container opposite at least a portion of the first outer portion; and detecting a level of a fluid contained in the container corresponding to the level sensor electrode. Each of the level sensor electrode and the common electrode has a conductive surface; and the applying and sensing are performed by a detection circuit.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments are directed to fluid containers used for fluid level detection, as well as a fluid level detection system and method for fluid containers.

To eliminate the above-described errors, a solution, according to an embodiment, is to integrate the electrodes or plates into a container design. This can be accomplished by using membrane switch technologies and using a MYLAR or other suitable thin sheet material, and conductively coating one side of the sheet. An adhesive backing may also be attached to the sheet, opposite the conductive surface, to secure it to the container. This sheet can also be used as the container identification and instructions-for-use label. Two of these sheets can be applied to the container on opposing walls. Upon placing the container, electrical contact to each conducting surface is made to a detection circuit. This approach yields high accuracy and precision for fluid level measurement. Reasonably exact values for fluid remaining in containers can be accomplished cost effectively and reliably (no moving parts). The container can also, according to an embodiment, be painted selectively with conductive inks to act as the electrodes, saving the cost of the sheet and adhesive.

For solid phase reagents, measurement of the capacitance before and after mixing may detect the change in dielectric constant, giving an indication of the percentage of suspended material. Information such as implements (probes) contacting the fluid surface and/or change in fluid level before/after pipetting, can be derived or recorded using this approach.

According to an embodiment, a radio-frequency identification (RFID) tag may be incorporated onto the container along with the level detection circuit. Energy to operate may be derived directly or inductively along with the data transfer to/from the host. This feature can be useful to record the container history, such as last used time event (e.g., date stamp), net evaporation during storage, re-suspension performance after storage, number of agitation cycles, instrument serial number, date opened/accessed, and other desirable information.

According to an embodiment, an end portion of each pack may interface to a connection and circuit to determine the fluid levels. The circuitry may also be integrated into an RFID type of system, as more fully described below. The connection points can also be on the top surface, according to an embodiment. Onboard reservoirs can be outfitted with this approach and then be monitored real time for active fluid levels. As the reservoirs are emptied, the levels and, thus the volume, of fluid taken would be available for confirmation of function of the instrument. Number of tests remaining and calls for replacement fluids can be determined and managed since this approach is accurate. The circuits (ICs) are available off-the-shelf; thus, the size and cost are small.

Figure 1A:
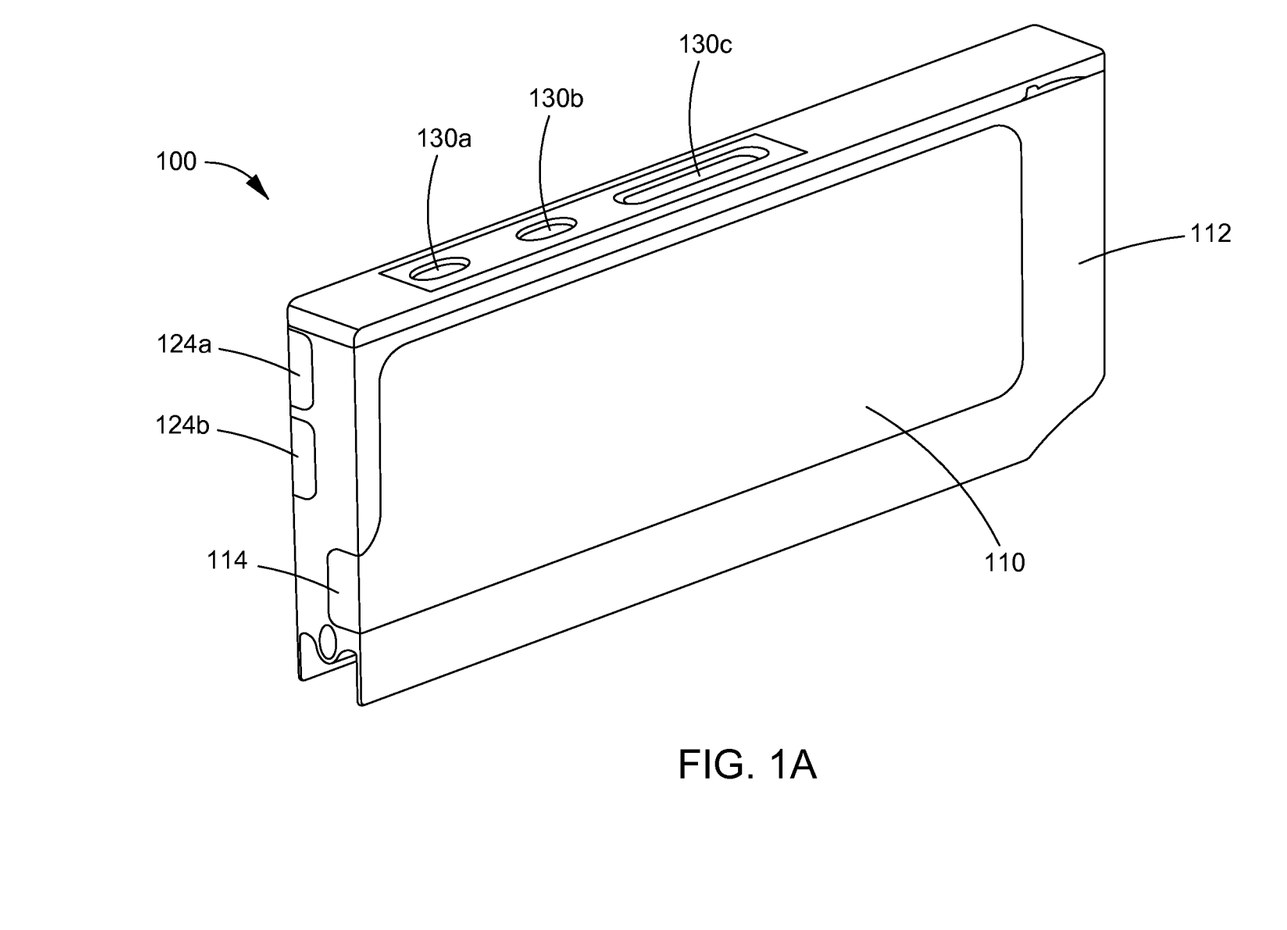
FIGS. 1A and 1B illustrate opposing sides of a fluid container used for fluid level detection, according to an embodiment.
Figure 1B:
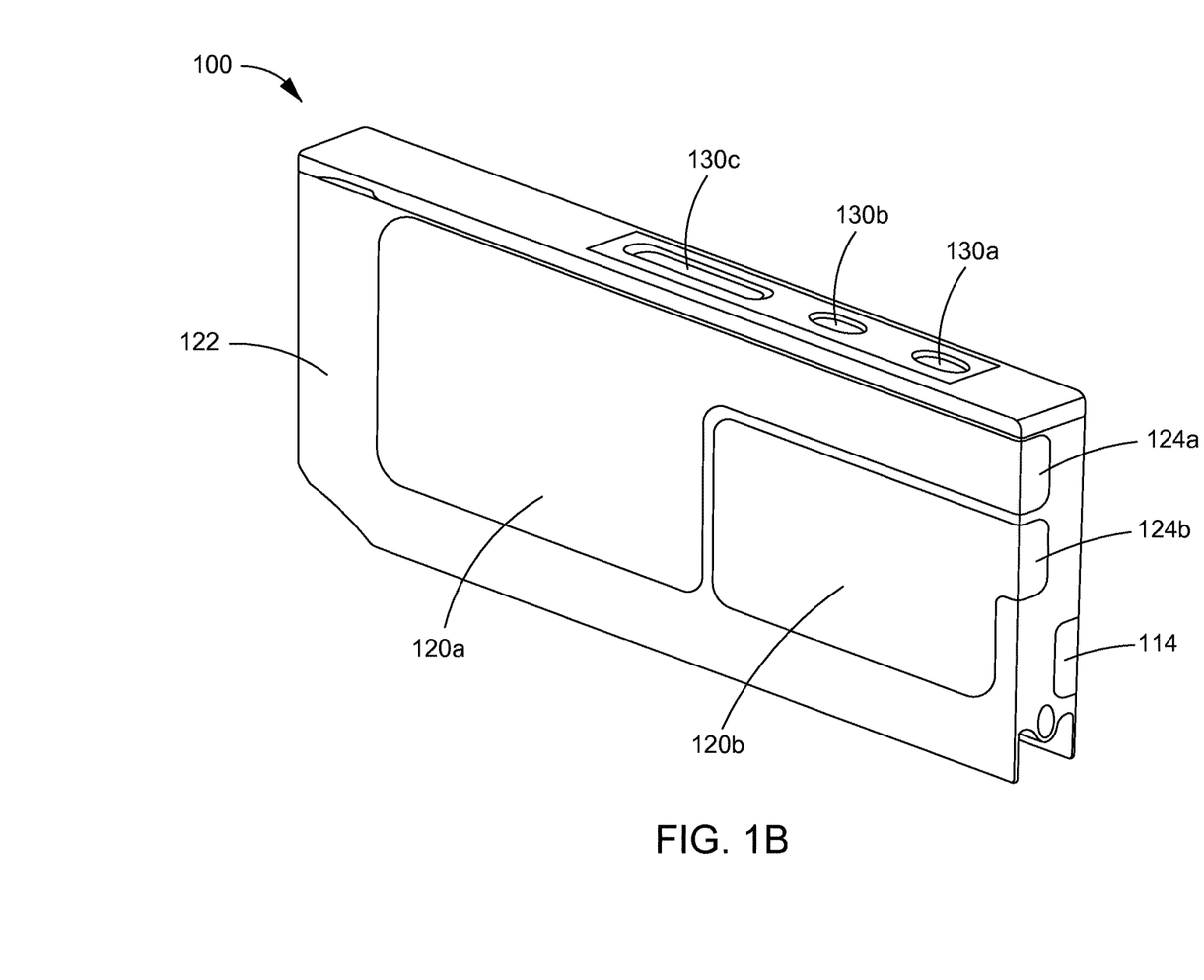

FIGS. 1A and 1B illustrate opposing sides of a fluid container 100 used for fluid level detection, according to an embodiment. The fluid container 100 includes one or more level sensor electrodes, each secured to a respective outer portion of the container 100. In the example embodiment shown in FIGS. 1A and 1B, two level sensor electrodes 120a and 120b are provided on outer portion 122 of the container 100 (see FIG. 1B); though fewer or additional level sensor electrodes may be provided. On the opposing side of the container 100 (see FIG. 1A) is outer portion 112 with a common electrode 110 secured thereto. The outer portion 112 with the common electrode 110 is opposite at least a portion of the outer portion 122 onto which the level sensor electrodes 120a, 120b are secured.

Each of the electrodes 110, 120a, and 120b comprise a conductive surface, which provides for a level detection of fluid in the container 100. More particularly, the container 100 is configured to come into contact with a circuit configured to apply a power source across one of the level sensor electrodes 120a or 120b and the common electrode 110 to thereby detect a level of fluid contained in the container 100 corresponding to the level sensor electrode 120a or 120b to which the power source is applied.

Thus, if, according to an embodiment, the container 100 includes a plurality of compartments within the container 100, and each of the level sensor electrodes 120a, 120b corresponds to a particular compartment, fluid level detection in a specific compartment may be achieved by applying a power source across the common electrode 110 and the level sensor electrode 120a or 120b corresponding to the specific compartment of interest.

As shown in FIGS. 1A and 1B, three openings 130a, 130b, and 130c are provided in the container 100 to allow for fluid insertion and extraction into and out of the container 100. The openings 130a, 130b, and 130c may provide access to one or more compartments of the container 100. Fewer or additional openings may be provided, according to other embodiments.

According to an embodiment, the conductive surfaces of each of the electrodes 110, 120a, and 120b comprise a thin sheet with a conductive coating applied thereto. According to an embodiment, an adhesive backing opposite the conductive surface may be provided, allowing for the electrodes 110, 120a, and 120b to be secured to the container 100 with the adhesive backing.

With continued reference to FIGS. 1A and 1B, the electrodes 110, 120a, and 120b may comprise a contact 114, 124a, and 124b, respectively, to which the power source is applied.

According to an embodiment, an RFID tag may be embedded in a level sensor electrode 120a or 120b to identify the level sensor electrode 120a or 120b, and to record and track data and information associated with the respective level sensor electrode 120a or 120b. In an embodiment, the RFID tag may be embedded in the contact 124a or 124b of the level sensor electrode 120a or 120b.

Figure 2:
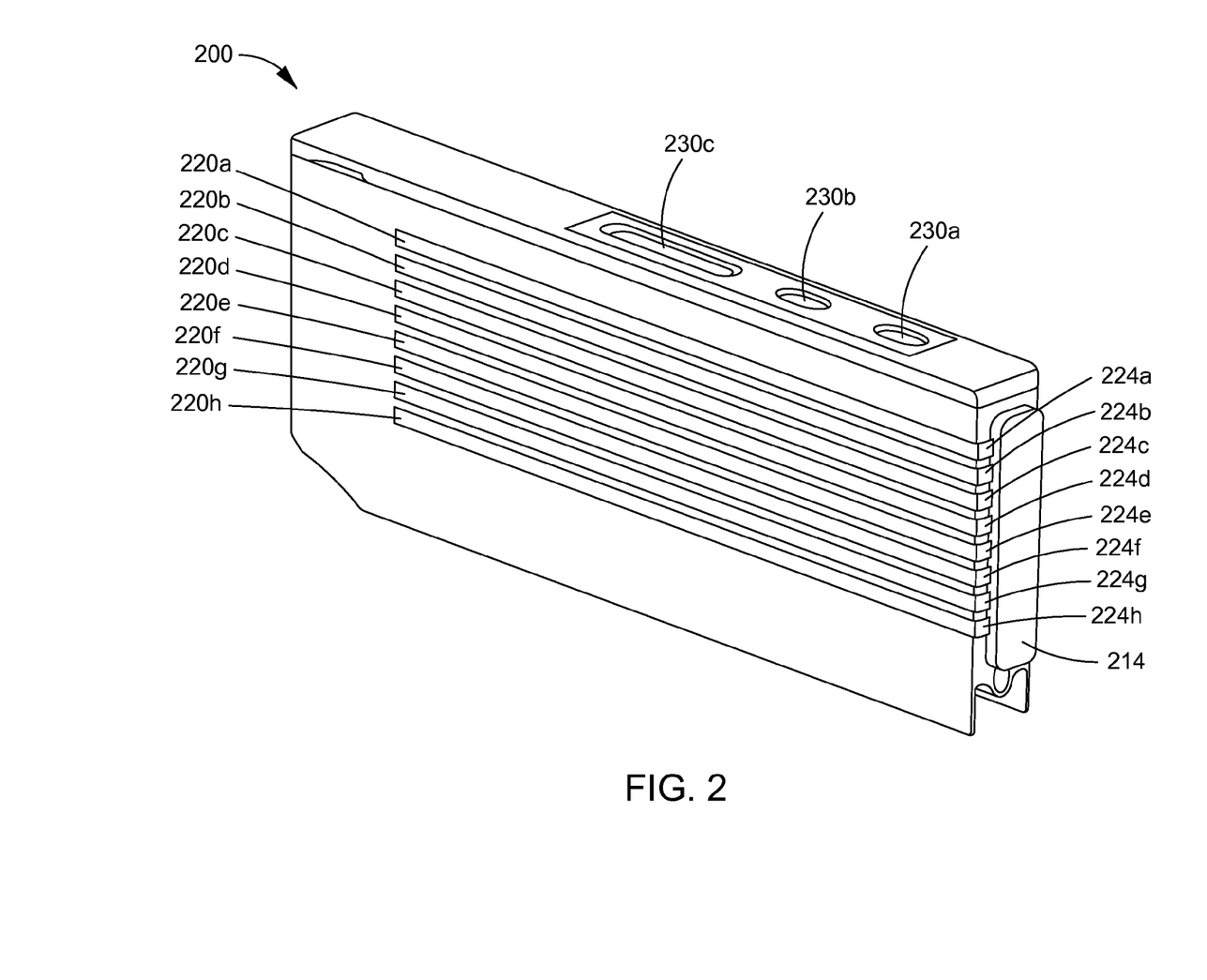
FIG. 2 is an exemplary fluid container used for fluid level detection, according to another embodiment.

FIG. 2 illustrates an exemplary fluid container 200 used for fluid level detection, according to another embodiment. The container 200 has a common electrode (not shown) with a contact 214 to which the power source is applied. The container 200 also has a plurality of level sensor electrodes 220a-220h with contacts 224a-224h, respectively. According to an embodiment, as shown, the level sensor electrodes 220a-220h are arranged in a substantially horizontal configuration along one side of the container 200, opposite the common electrode. By applying a power source to the common electrode and one of the level sensor electrodes

220a-220h, a dielectric constant is detected at a horizontal position of the container 200 corresponding to the level sensor electrode 220a-220h at which the power source is applied, thus providing a detection of fluid level at the horizontal position.

According to an embodiment, the container 200 may include a plurality of compartments within the container 200. Detection of the dielectric constant at the horizontal position of the container 200 comprises detection in one of the plurality of compartments corresponding to one of the plurality of level sensor electrodes 220a-220h to which the power source is applied.

As shown in FIG. 2, three openings 230a, 230b, and 230c are provided in the container 200 to allow for fluid insertion and extraction into and out of the container 200. The openings 230a, 230b, and 230c may provide access to one or more compartments of the container 200. Fewer or additional openings may be provided.

Figure 3:
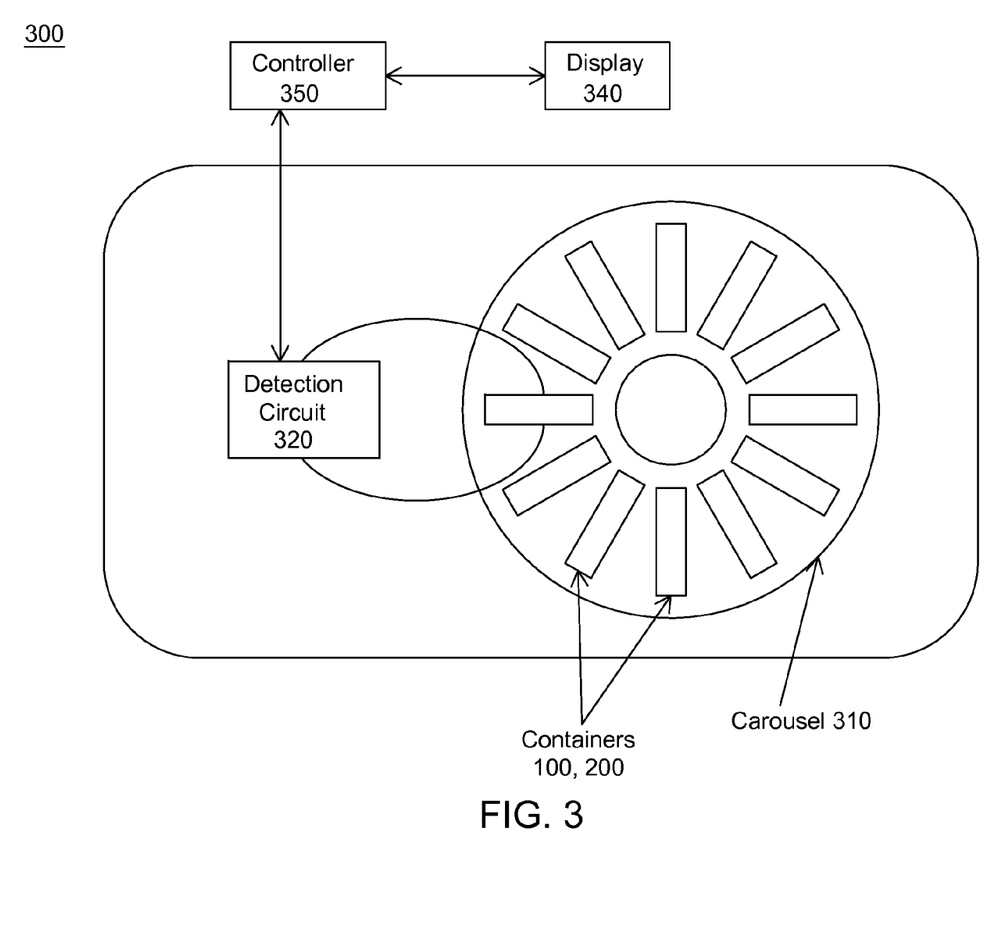
FIG. 3 illustrates a fluid level detection system for fluid containers, according to an embodiment.

FIG. 3 illustrates a fluid level detection system 300 for fluid containers, according to an embodiment. The containers 100, 200 may be arranged on a carousel 310. A detection circuit 320 is provided for applying the power source across the common electrode 110 and the level sensor electrode 120a or 120b of interest (or the common electrode and the level sensor electrode 220a-220h of interest) to detect a level of fluid contained in the container 100 (or 200) corresponding to the level sensor electrode to which the power source is applied.

In an embodiment, the detection circuit 320 is disposed in a location accessible to a plurality of containers 100, 200 in a diagnostic instrument.

The detection circuit 320 is, according to an embodiment, connected to and is in communication with a controller 350, configured to generate an indication of the detected level of fluid as detected by the detected circuit 320.

A display 340 may also be included. The display 340 is connected to the controller 350 and configured to display the indication of the detected level of fluid.

As noted above, one or more RFID tags may be provided, each embedded in a respective one of the one or more level sensor electrodes 120a, 120b, 220a-220h to identify the respective one of the one or more level sensor electrodes. The controller 350, according to an embodiment, may be configured to associate and store data relating to the one or more level sensor electrodes 120a, 120b, 220a-220h based upon the identification with a respective one of the one or more RFID tags.

Figure 4:
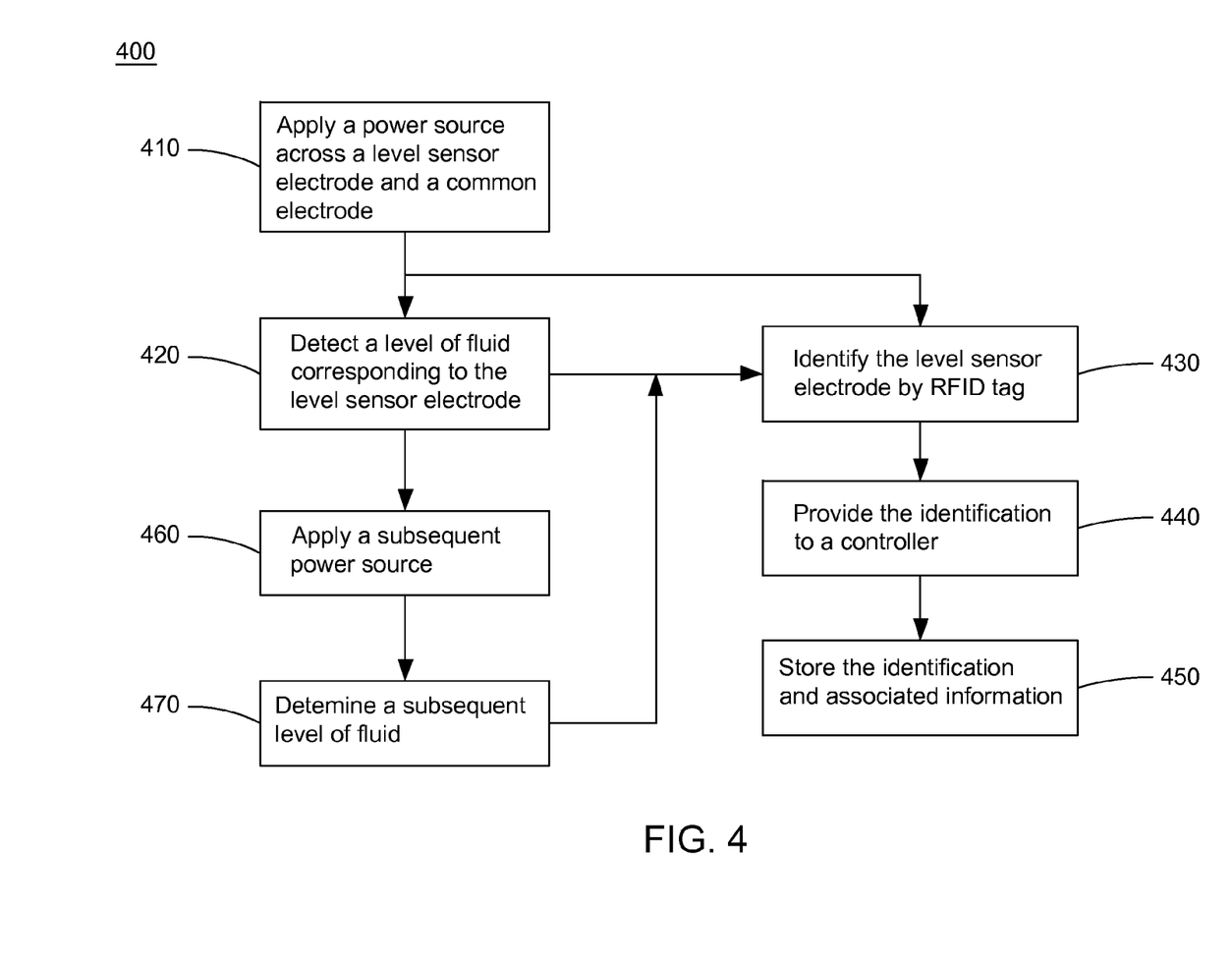
FIG. 4 is a flowchart illustrating a method of detecting a fluid level in a container, according to an embodiment.

FIG. 4 is a flowchart 400 illustrating a method of detecting a fluid level in a container, according to an embodiment.

At 410, a power source is applied across a level sensor electrode 120a or 120b (or 220a-220h) and a common electrode 110 of a container 100 (or the common electrode of container 200). At 420, a level of fluid corresponding to the level sensor electrode 120a or 120b (or 220a-220h) is detected by, for example, a detection circuit 320.

At 430, following the power source being applied at 410 and/or the level of fluid being detected at 420, the level sensor electrode 120a or 120b (or 220a-220h) is identified by its embedded RFID tag. At 440, the identification is provided to the controller 350; and at 450, the identification and associated information relating to the container 100 (or 200) and the fluid level detection is stored.

According to an embodiment, at 460, following the level of fluid being detected at 420, a subsequent power source is applied across the level sensor electrode 120a or 120b (or 220a-220h) and the common electrode 110 of the container 100 (or the common electrode of container 200). At 470, a subsequent level of fluid corresponding to the level sensor electrode 120a or 120b (or 220a-220h) is detected. The process of identifying the level sensor electrode (430), providing the identification to the controller (440), and storing the identification and associated information (450) may be repeated. This provides for identifying how the fluid level has changed over a given time period. For example, this process may be used to confirm aspiration of fluid from one of the compartments of the container 100 or 200.

Figure 5:
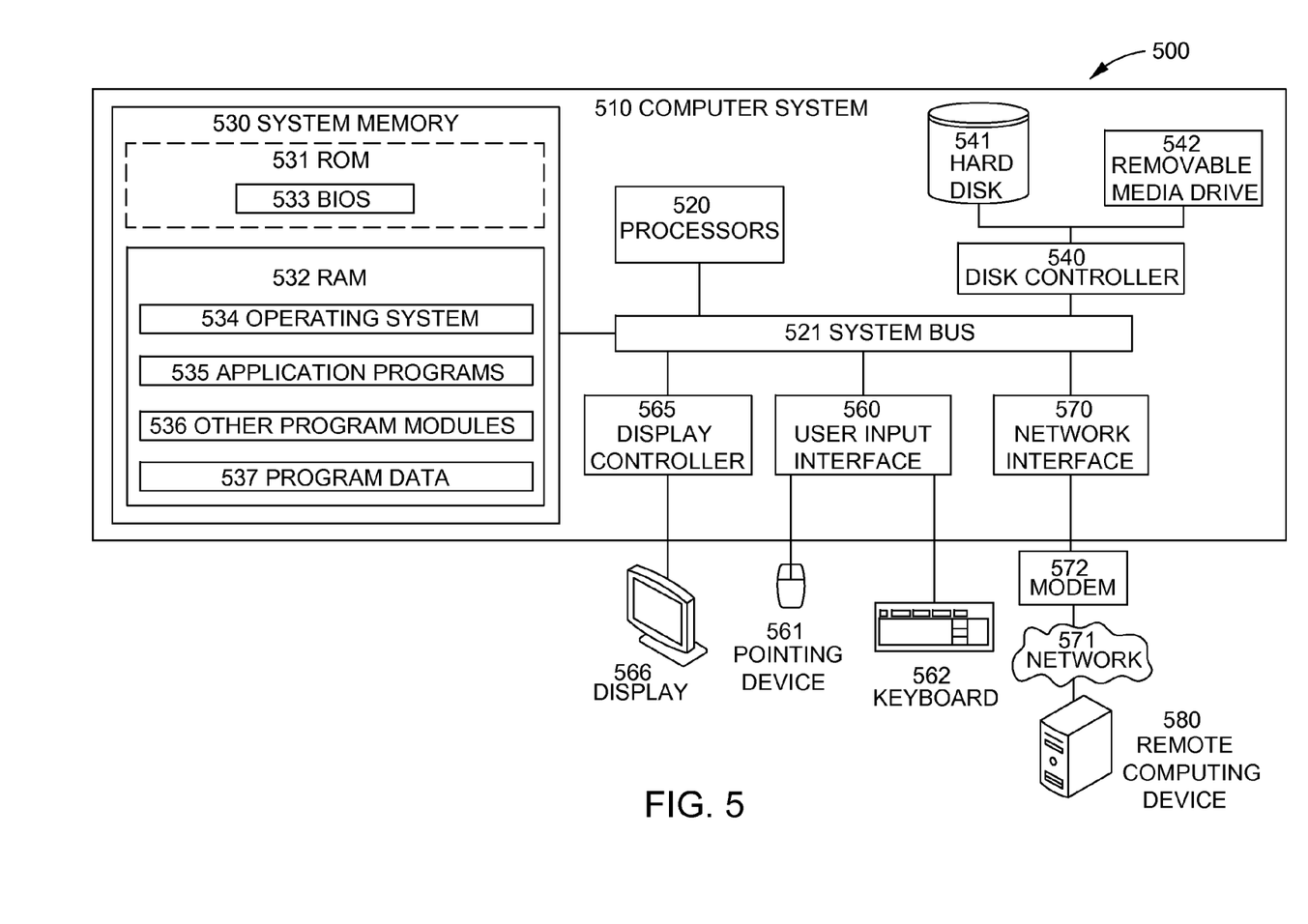
FIG. 5 illustrates an exemplary computing environment within which embodiments of the invention may be implemented.

FIG. 5 illustrates an exemplary computing environment 500 within which embodiments of the invention may be implemented. Computing environment 500 may include computer system 510, which is one example of a general purpose computing system upon which embodiments of the invention may be implemented. Computers and computing environments, such as computer 510 and computing environment 500, are known to those of skill in the art and thus are described briefly here.

As shown in FIG. 5, the computer system 510 may include a communication mechanism such as a bus 521 or other communication mechanism for communicating information within the computer system 510. The system 510 further includes one or more processors 520 (such as the controller 350 described above) coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a magnetic hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display or monitor 566, such as a cathode ray tube (CRT) or liquid crystal display (LCD), for displaying information to a computer user. The computer system 510 includes an input interface 560 and one or more input devices, such as a keyboard 562 and a pointing device 561, for interacting with a computer user and providing information to the processors 520. The pointing device 561, for example, may be a mouse, a trackball, or a pointing stick for communicating direction information and command selections to the processors 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more data-stores and data files used by embodiments of the present invention. Data-store contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according embodiments of the invention and for containing data structures, tables, records, or other data described herein. The term "computer readable medium" as used herein refers to any medium that participates in providing instructions to the processors 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to system bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computing system 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

The invention claimed is:

1. A fluid level detection system for fluid containers, comprising:
    a container configured to hold one or more fluids;
    one or more level sensor electrodes, each secured to a first side of the container;
    a common electrode secured to a second side of the container, wherein the first side is opposite to the second side;
    a detection circuit configured to apply a power source across one of the one or more level sensor electrodes and the common electrode to detect a level of fluid of the one or more fluids contained in the container corresponding to the one of the one or more level sensor electrodes; and
    one or more radio-frequency identification tags, each embedded in a respective one of the one or more level sensor electrodes to identify the respective one of the one or more level sensor electrodes,
    wherein each of the one or more level sensor electrodes and the common electrode comprises a conductive surface.

2. The system of claim 1, wherein the container comprises a plurality of compartments, wherein the one or more level sensor electrodes comprise a plurality of level sensor electrodes, each secured on the container to correspond to a respective one of the plurality of compartments.

3. The system of claim 1, wherein the one or more level sensor electrodes and the common electrode each comprise a contact to which the power source is applied.

4. The system of claim 1, wherein the conductive surfaces each comprise a thin sheet with a conductive coating applied thereto.

5. The system of claim 1, wherein each of the one or more level sensor electrodes and the common electrode comprises an adhesive backing opposite the conductive surface, and wherein each of the one or more level sensor electrodes and the common electrode is secured to the container with the adhesive backing.

6. The system of claim 1, wherein the detection circuit is disposed in a location accessible to a plurality of containers in a diagnostic instrument.

7. The system of claim 1, further comprising:
a controller in communication with the detection circuit and configured to generate an indication of the detected level of fluid.

8. The system of claim 7, further comprising:
a display connected to the controller and configured to display the indication of the detected level of fluid.

9. The system of claim 7,
wherein the controller is configured to associate and store data relating to the one or more level sensor electrodes based upon the identification with a respective one of the one or more radio-frequency identification tags.

10. The system of claim 9, wherein each of the one or more radio-frequency identification tags is embedded in respective contacts of the one or more level sensor electrodes.

11. The system of claim 1, wherein the one or more level sensor electrodes comprise a plurality of level sensor electrodes arranged in a substantially horizontal configuration along the container; and
wherein contact with the detection circuit applying the power source causes detection of a dielectric constant at a horizontal position of the container corresponding to the level sensor electrode at which the power source is applied.

12. The system of claim 11, wherein the container comprises a plurality of compartments, each with an associated one of the plurality of level sensor electrodes, wherein the detection of the dielectric constant at the horizontal position comprises detection in one of the plurality of compartments corresponding to the associated one of the plurality of level sensor electrodes to which the power source is applied.

13. A fluid container for fluid level detection, comprising:
one or more level sensor electrodes, each secured to a respective outer portion of the container;
a common electrode secured to a second outer portion of the container, the second outer portion of the container opposite at least a portion of each of the respective outer portions of the one or more level sensor electrodes; and
one or more radio-frequency identification tags, each embedded in a respective one of the one or more level sensor electrodes to identify the respective one of the one or more level sensor electrodes,
wherein each of the one or more level sensor electrodes and the common electrode comprises a conductive surface; and
wherein the container is configured to come into contact with a circuit configured to apply a power source across one of the one or more level sensor electrodes and the common electrode to detect a level of fluid contained in the container corresponding to the one of the one or more level sensor electrodes.

14. The container of claim 13, further comprising:
a plurality of compartments;
wherein the one or more level sensor electrodes comprise a plurality of level sensor electrodes, each secured on the container to correspond to a respective one of the plurality of compartments.

15. The container of claim 13, wherein the one or more level sensor electrodes and the common electrode each comprise a contact to which the power source is applied.

16. The container of claim 13, wherein the conductive surfaces each comprise a thin sheet with a conductive coating applied thereto.

17. The container of claim 13, wherein each of the one or more level sensor electrodes and the common electrode comprises an adhesive backing opposite the conductive surface, and wherein each of the one or more level sensor electrodes and the common electrode is secured to the container with the adhesive backing.

18. The container of claim 13, wherein each of the one or more radio-frequency identification tags is embedded in respective contacts of the one or more level sensor electrodes.

19. The container of claim 13, wherein the one or more level sensor electrodes comprise a plurality of level sensor electrodes, the plurality of level sensor electrodes arranged in a substantially horizontal configuration along the container; and
wherein contact with the circuit applying the power source detects a dielectric constant at a horizontal position of the container corresponding to the level sensor electrode at which the power source is applied.

20. The container of claim 19, further comprising a plurality of compartments, each with an associated one of the plurality of level sensor electrodes, wherein the detection of the dielectric constant at the horizontal position comprises detection in one of the plurality of compartments corresponding to the associated one of the plurality of level sensor electrodes to which the power source is applied.

21. A method of detecting a fluid level in a container, comprising:
applying a power source across a level sensor electrode and a common electrode, the level sensor electrode secured to a first side of the container and the common electrode secured to a second side of the container, wherein the first side is opposite to the second side;
detecting a level of a fluid contained in the container corresponding to the level sensor electrode; and
identifying one of the plurality of level sensor electrodes by a radio-frequency identification tag embedded in the respective one of the plurality of level sensor electrodes;
wherein each of the level sensor electrode and the common electrode have a conductive surface; and
wherein the applying and sensing are performed by a detection circuit.

22. The method of claim 21, wherein the container comprises a plurality of compartments, wherein a plurality of level sensor electrodes are each secured to a respective outer portion on the first side of the container to correspond to a respective one of the plurality of compartments;
wherein the power source is applied across one of the plurality of level sensor electrodes and the common electrode to detect a level of the fluid contained in the container corresponding to the one of the plurality of level sensor electrodes.

23. The method of claim 22, further comprising:
providing the identification of the one of the plurality of level sensor electrodes to a controller in communication with the detection circuit and the radio-frequency identification tag, wherein the controller is configured to generate an indication of the detected level of fluid and store data relating to the one of the plurality of level sensor electrodes based upon the identification.

24. The method of claim 23, further comprising:
applying a subsequent power source across the corresponding one of the plurality of level sensor electrodes and the common electrode to detect a subsequent level of the fluid in the one of the plurality of compartments;

determining if the subsequent level is less than the level of the fluid; and storing information relating to the determination of the subsequent level through a corresponding radio-frequency identification tag.

25. The method of claim 21, wherein each of the level sensor electrode and the common electrode comprises an adhesive backing opposite the conductive surface, and wherein each of the level sensor electrode and the common electrode is secured to the container with the adhesive backing.

\* \* \* \* \*